United States Patent [19]

Sauer et al.

[11] Patent Number: 5,562,686
[45] Date of Patent: Oct. 8, 1996

[54] APPARAUS AND METHOD FOR SUTURING BODY TISSUE

[75] Inventors: Jude S. Sauer, Pittsford; Roger J. Greenwald, Holley; Theodore J. Tiberio, Hilton; Jeffrey M. Shaw, Livonia; John F. Hammond, Canandaiqua, all of N.Y.; Peter W. J. Hinchliffe, New Haven, Conn.

[73] Assignee: United States Surgical Corporation, Norwalk, Conn.

[21] Appl. No.: 424,946

[22] Filed: Apr. 19, 1995

[51] Int. Cl.$^6$ .................................................. A61B 17/00
[52] U.S. Cl. ........................... 606/144; 606/148; 112/169
[58] Field of Search .................................. 606/139, 144, 606/145, 147, 148; 112/169, 80.03

[56] References Cited

U.S. PATENT DOCUMENTS

| | | |
|---|---|---|
| 659,422 | 10/1900 | Shidler . |
| 1,037,864 | 9/1912 | Carlson et al. . |
| 1,822,330 | 9/1931 | Ainslie . |
| 2,601,564 | 6/1952 | Smith . |
| 2,880,728 | 4/1959 | Rights . |
| 3,168,097 | 2/1965 | Dormia . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer . |
| 4,164,225 | 8/1979 | Johnson et al. . |
| 4,493,323 | 1/1985 | Albright et al. . |
| 4,827,931 | 5/1989 | Longmore . |
| 4,841,888 | 6/1989 | Mills et al. . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 5,047,039 | 9/1991 | Avant et al. . |
| 5,080,663 | 1/1992 | Mills et al. . |
| 5,261,918 | 11/1993 | Phillips et al. ........................ 606/140 |
| 5,364,408 | 11/1994 | Gordon . |
| 5,368,601 | 11/1994 | Sauer et al. . |
| 5,403,328 | 4/1995 | Shallman . |
| 5,425,737 | 6/1995 | Burbank et al. ....................... 606/144 |
| 5,431,666 | 7/1995 | Sauer et al. ............................ 606/144 |
| 5,454,822 | 10/1995 | Schöb et al. .......................... 606/148 |
| 5,476,470 | 12/1995 | Fitzgibbons, Jr. ..................... 606/148 |

FOREIGN PATENT DOCUMENTS

| | | |
|---|---|---|
| 0140557 | 5/1985 | European Pat. Off. . |
| 4137218 | 2/1993 | Germany . |
| 1093329 | 5/1984 | U.S.S.R. . |
| 9106247 | 5/1991 | WIPO . |
| 9301750 | 4/1993 | WIPO . |
| WO/94/17737 | 8/1994 | WIPO ................................. 606/144 |

OTHER PUBLICATIONS

REMA Brochure, Germany.

*Primary Examiner*—Michael Powell Buiz
*Assistant Examiner*—Jeffrey A. Schmidt

[57] ABSTRACT

An apparatus for suturing body tissue is provided having an elongated housing, first and second jaws pivotably mounted to the distal portion of elongated housing, and first and second needles movable with respect to the first and second jaws. A first actuating mechanism is operatively associated with the first and second jaws such that actuation moves the jaws from the first position to a second position. A second actuating mechanism is operatively associated with the first and second needles wherein actuation advances the first and second needles into body tissue. Each of the jaws has a recess for receiving body tissue and a ferrule attached to each end of the suture such that advancement of the needles engages the ferrule to pull the ferrule and suture through the body tissue when the needle is retracted.

34 Claims, 16 Drawing Sheets

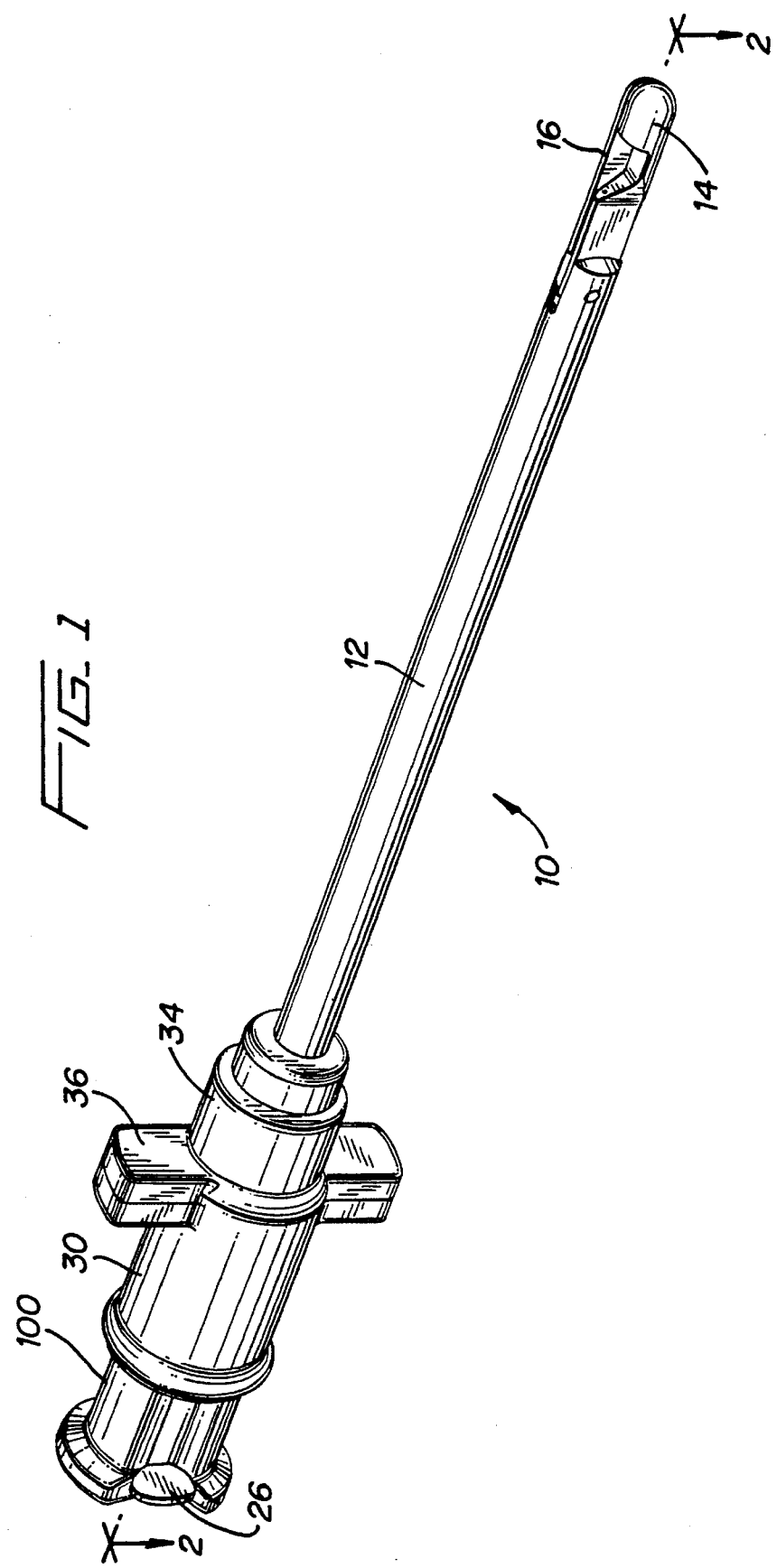

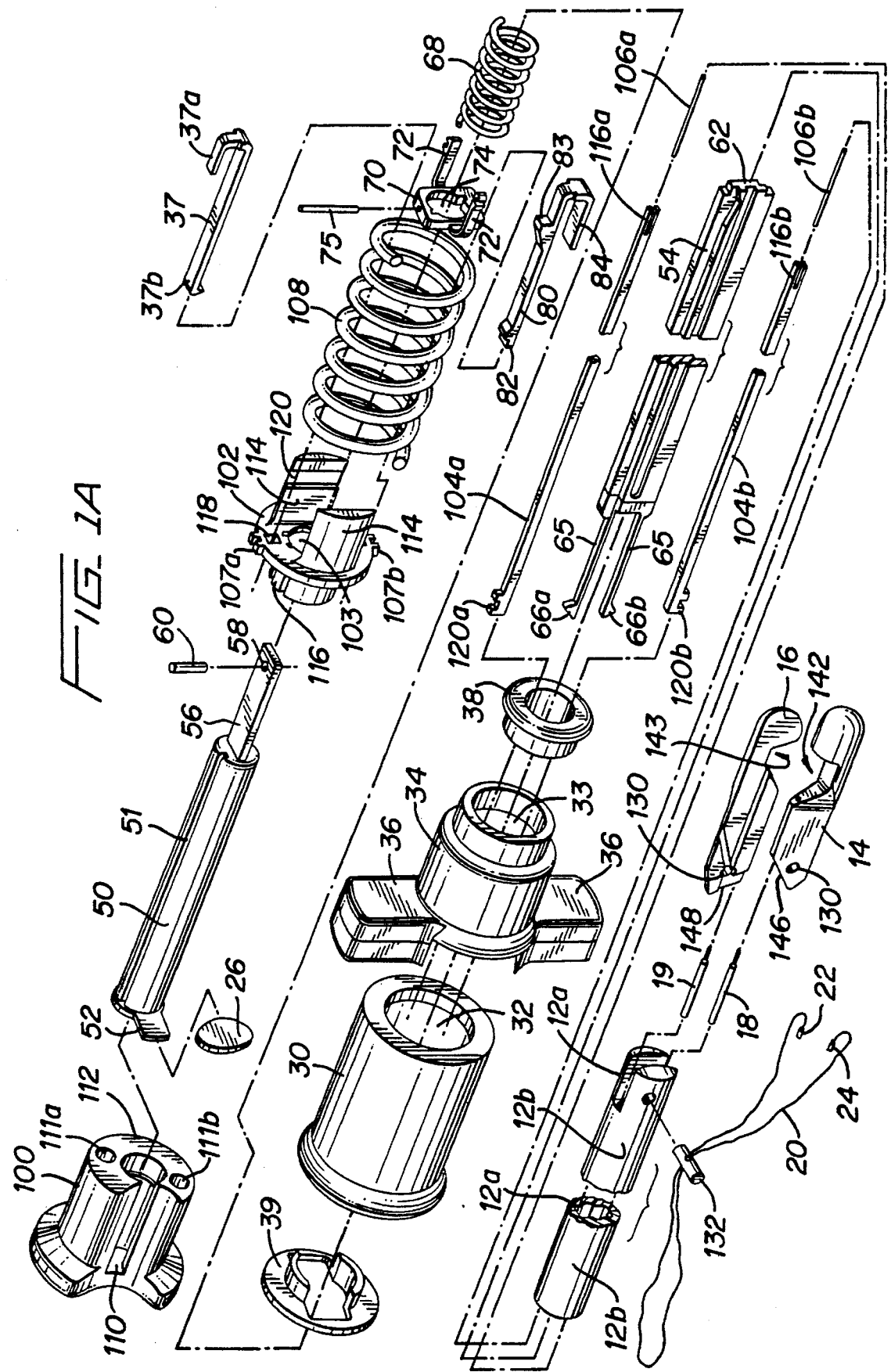

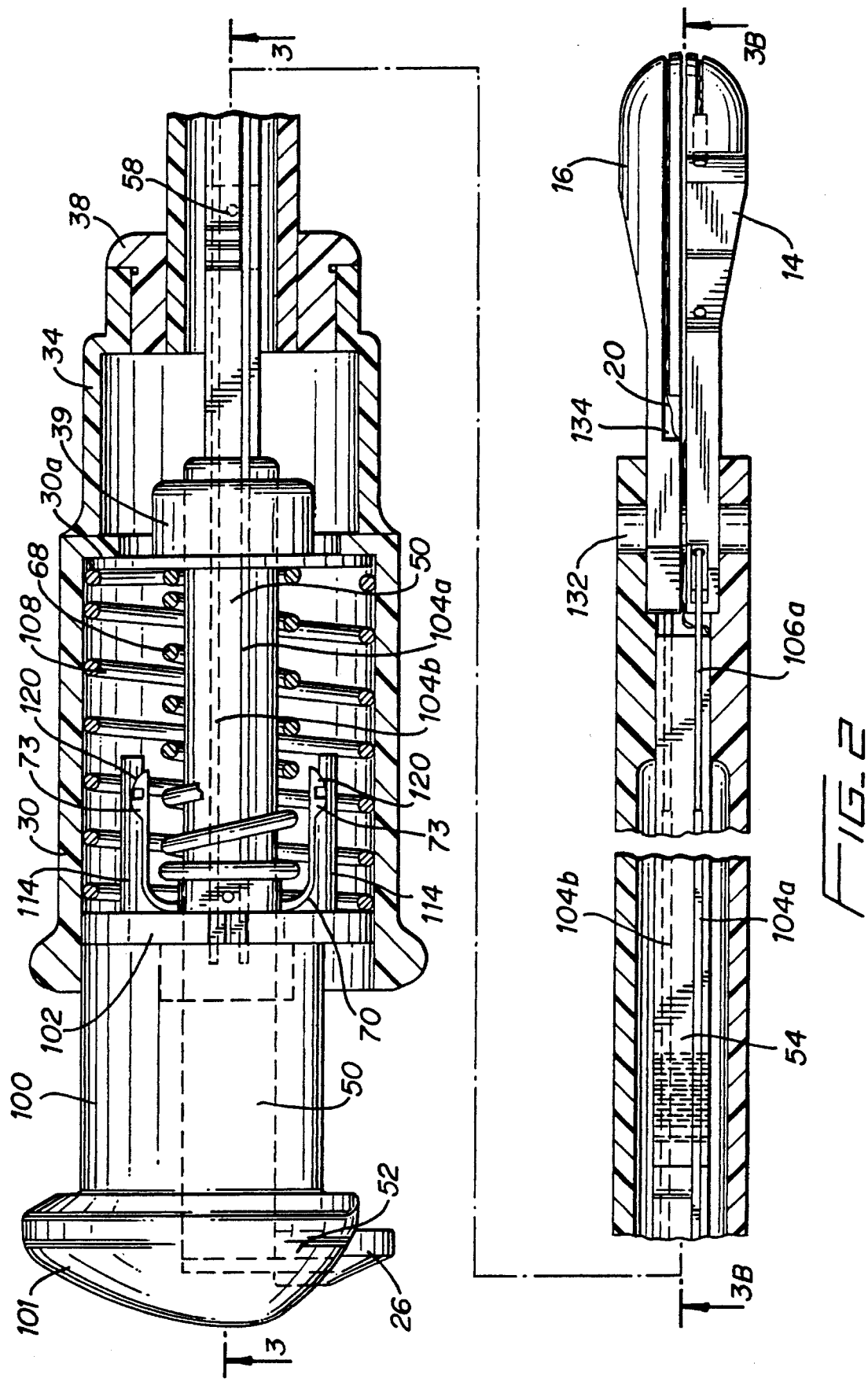

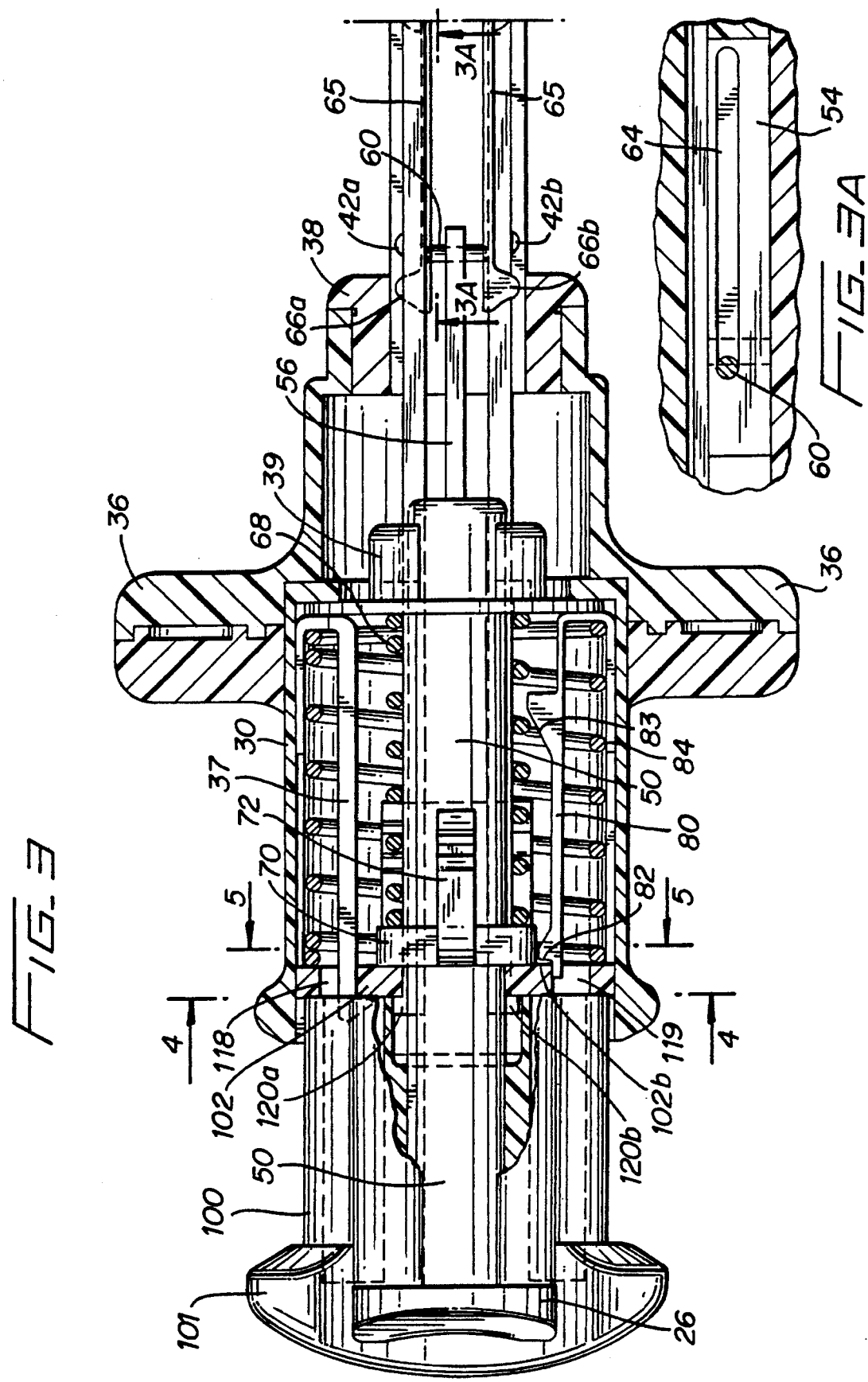

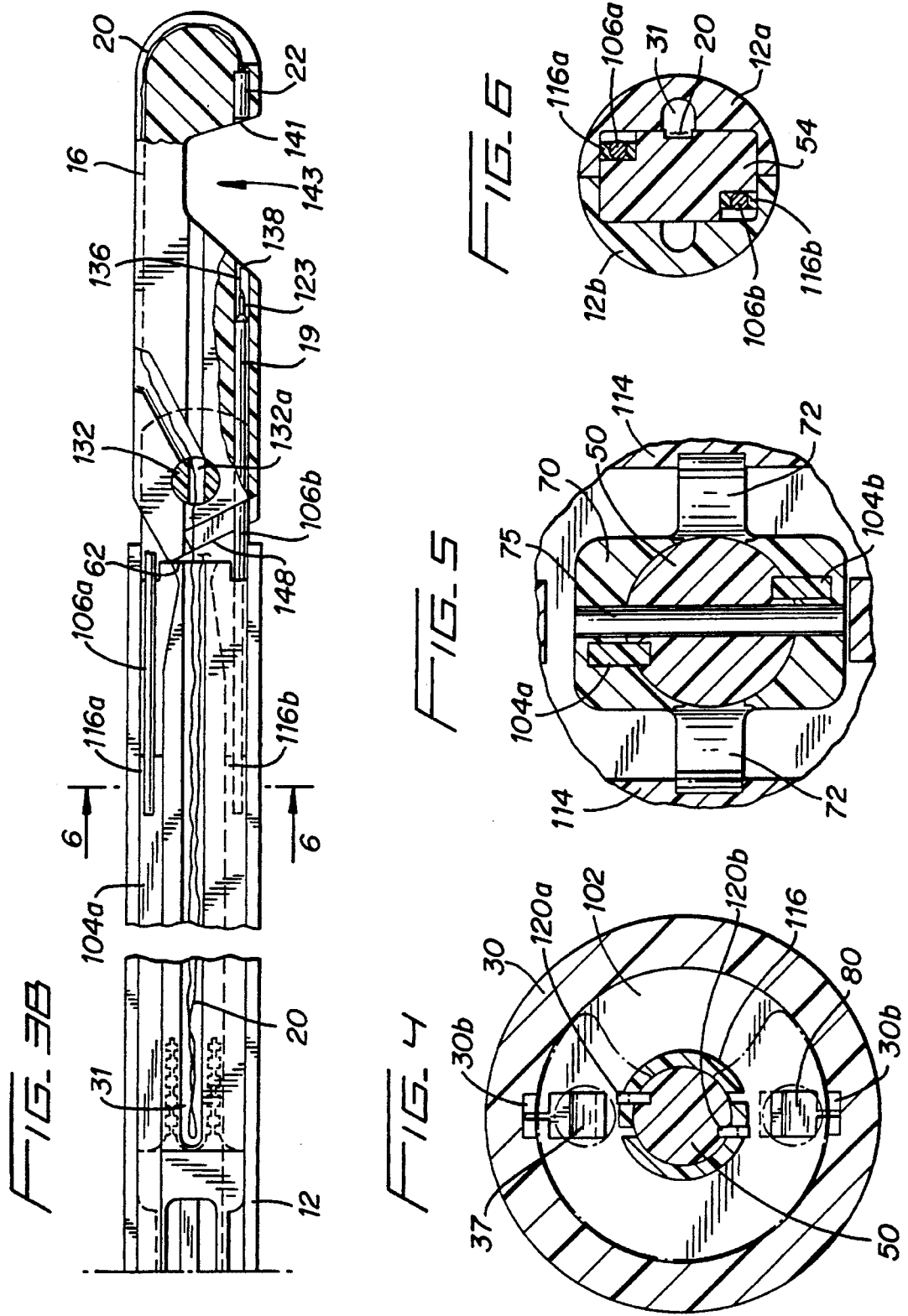

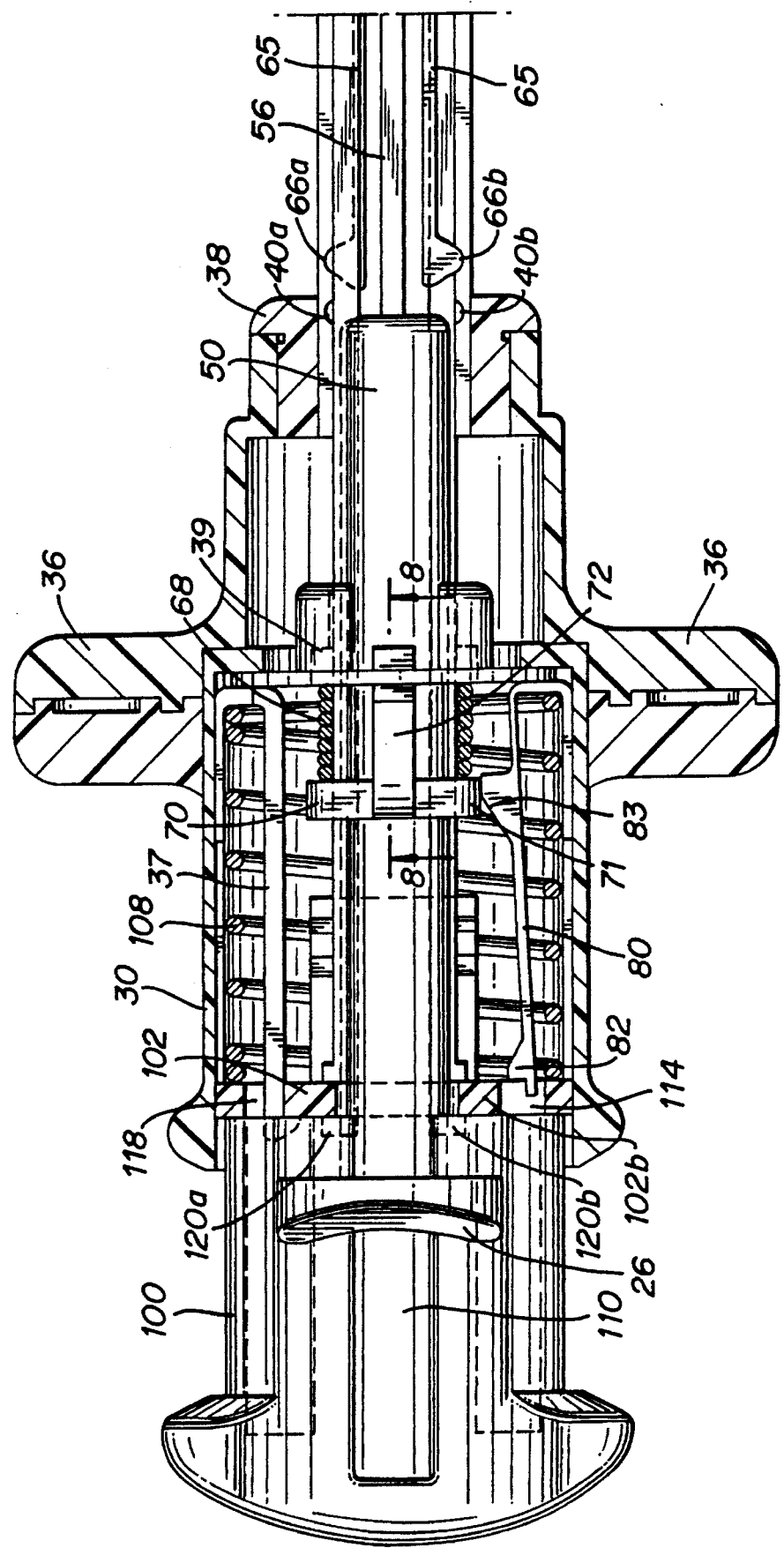

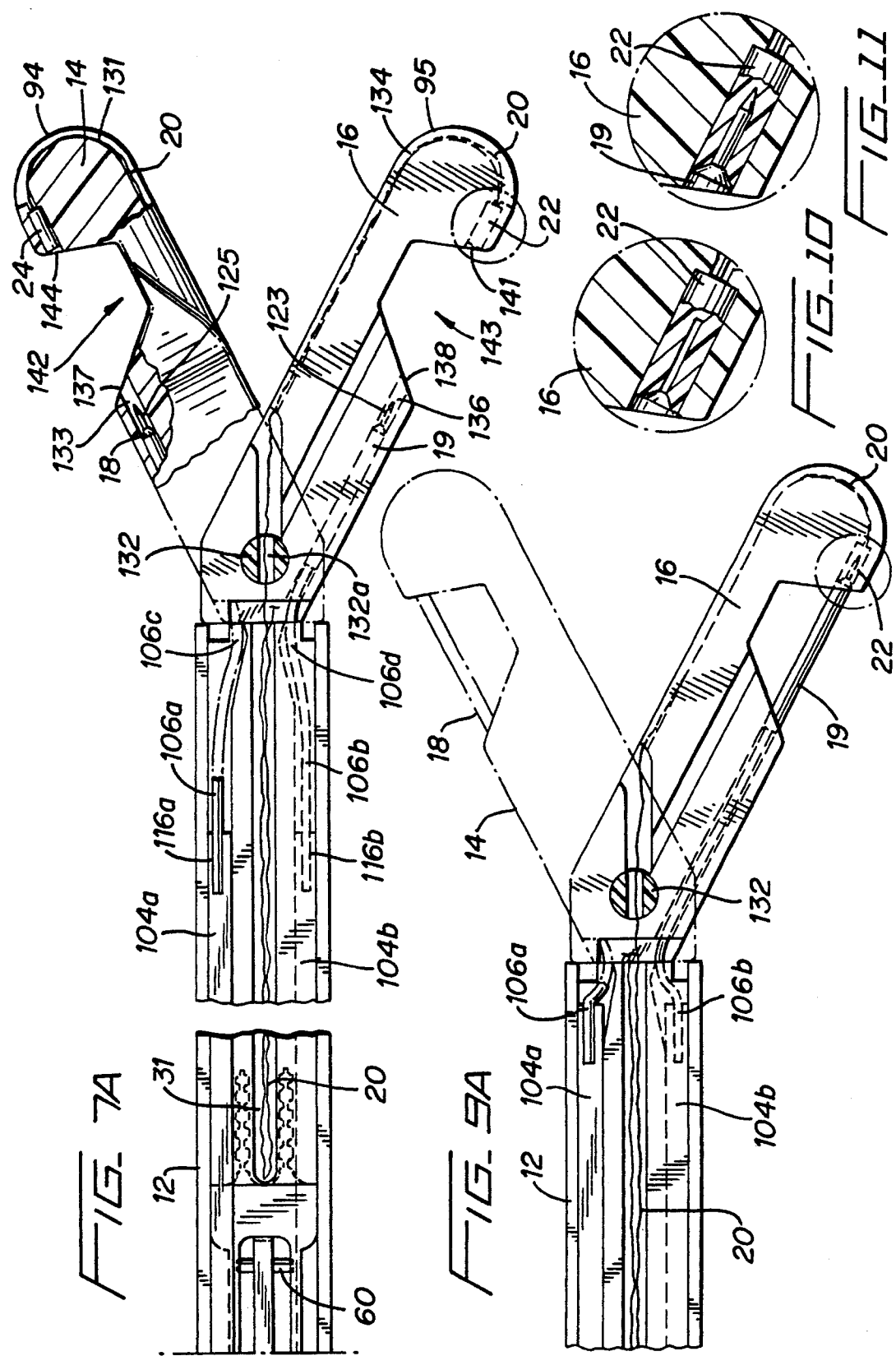

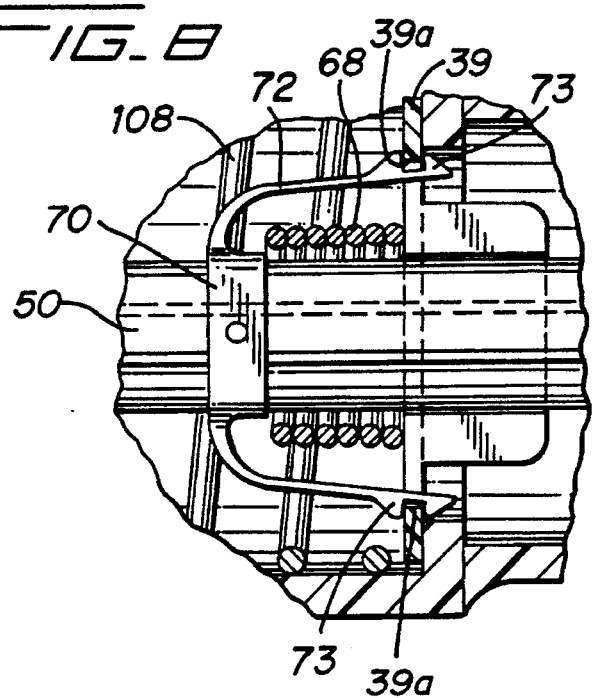
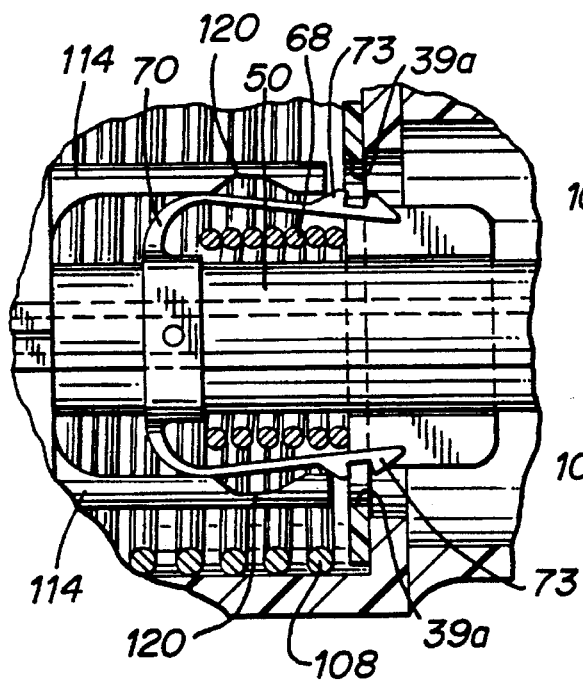
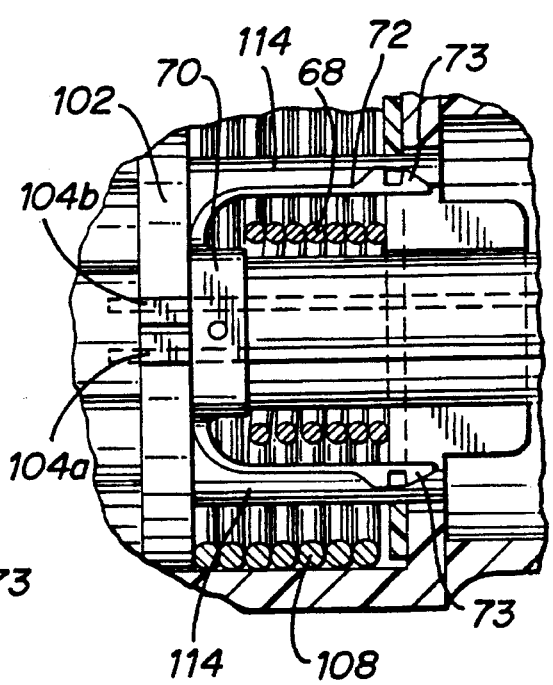

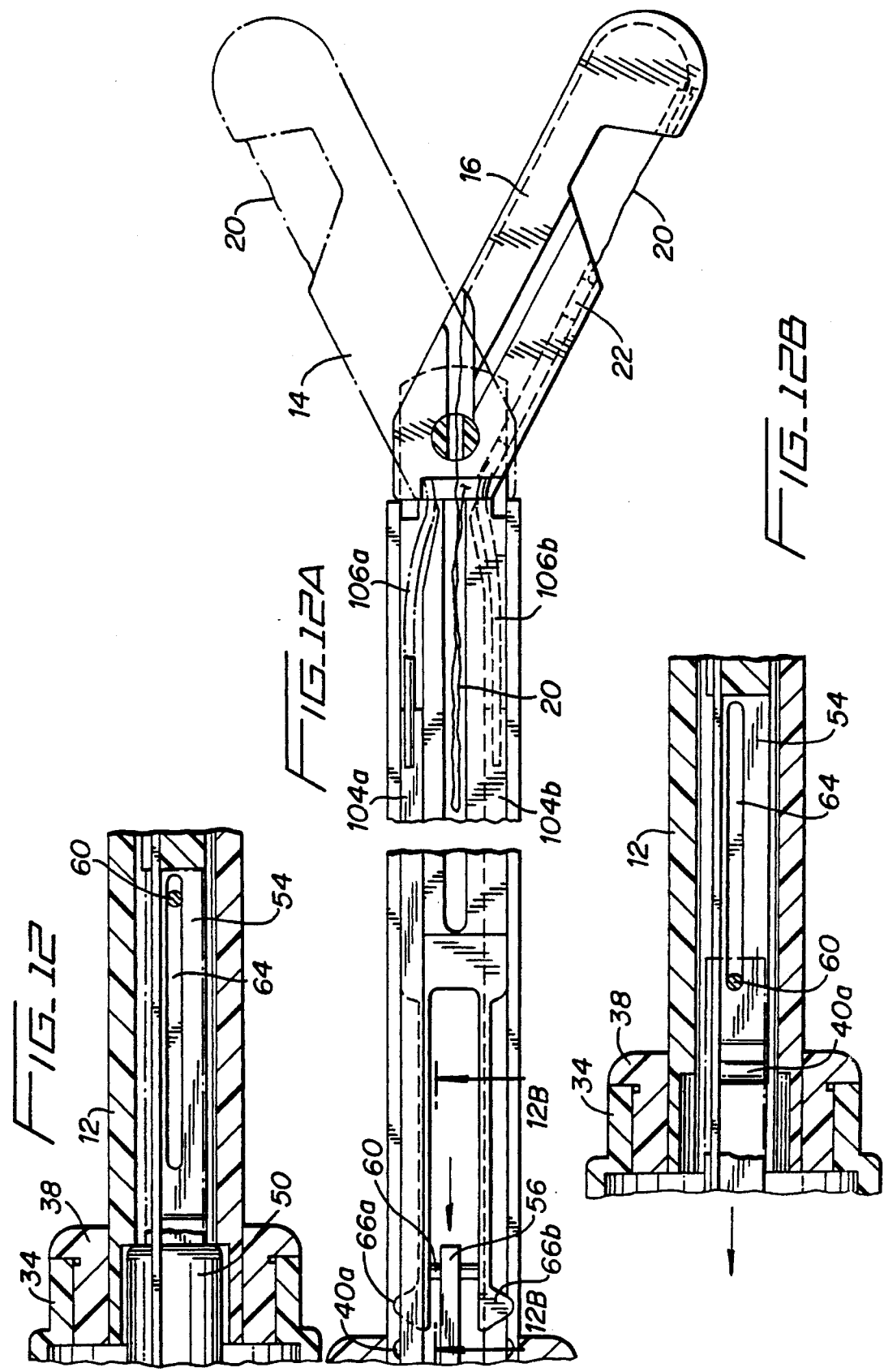

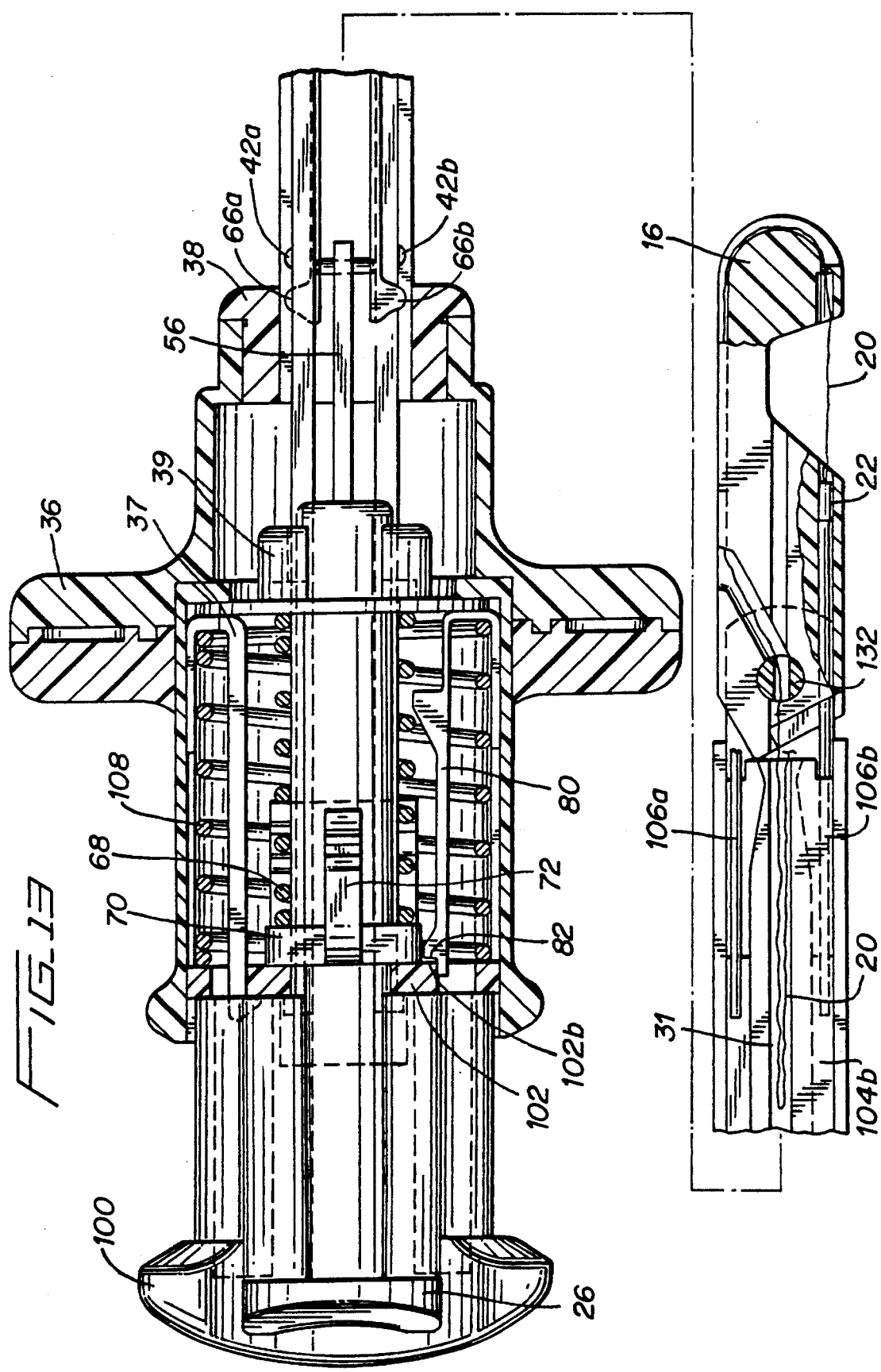

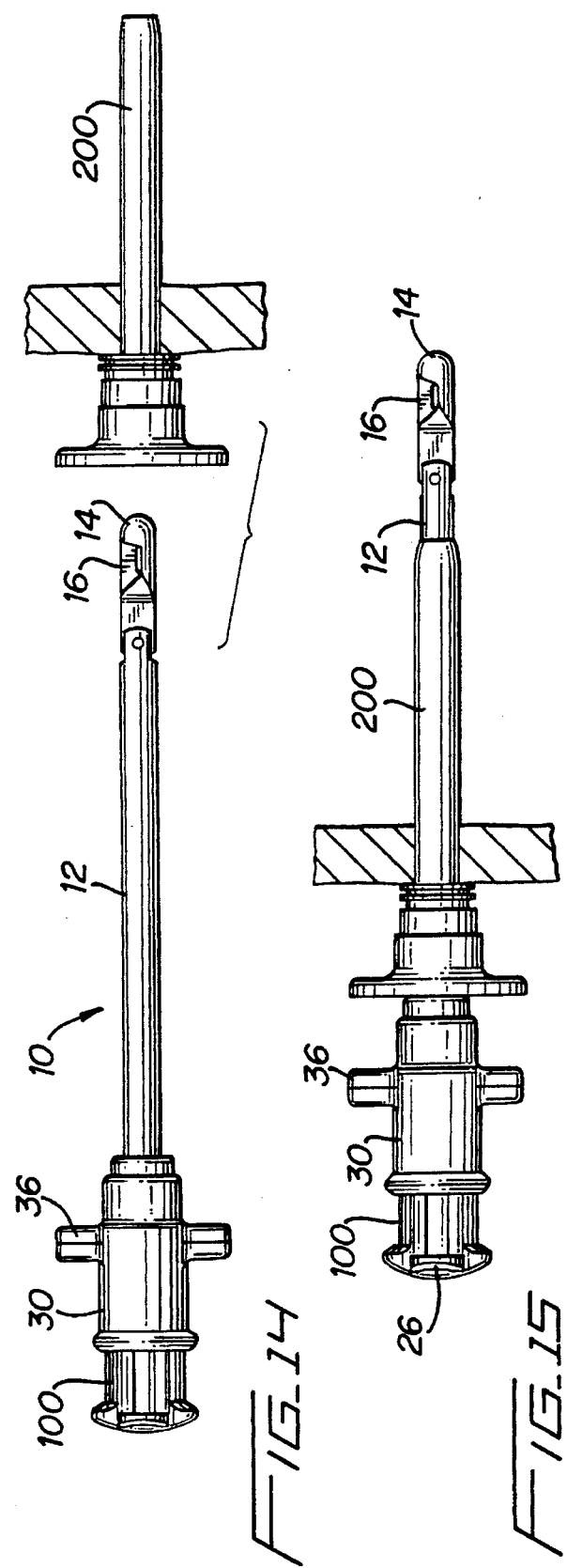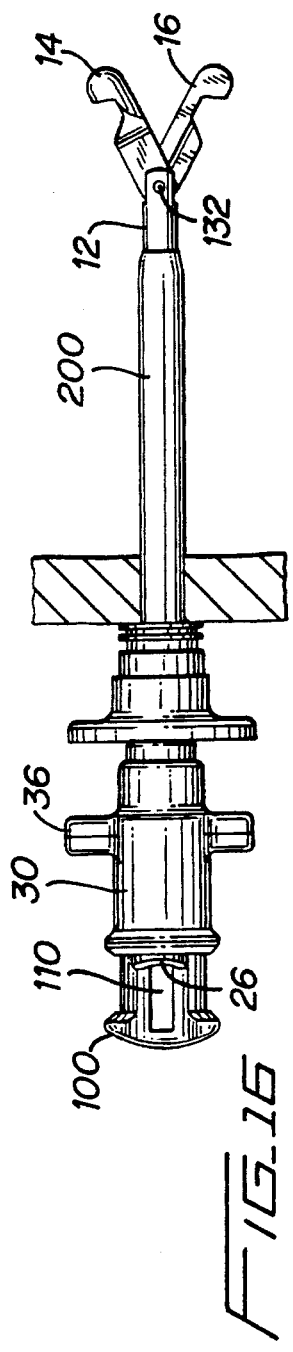

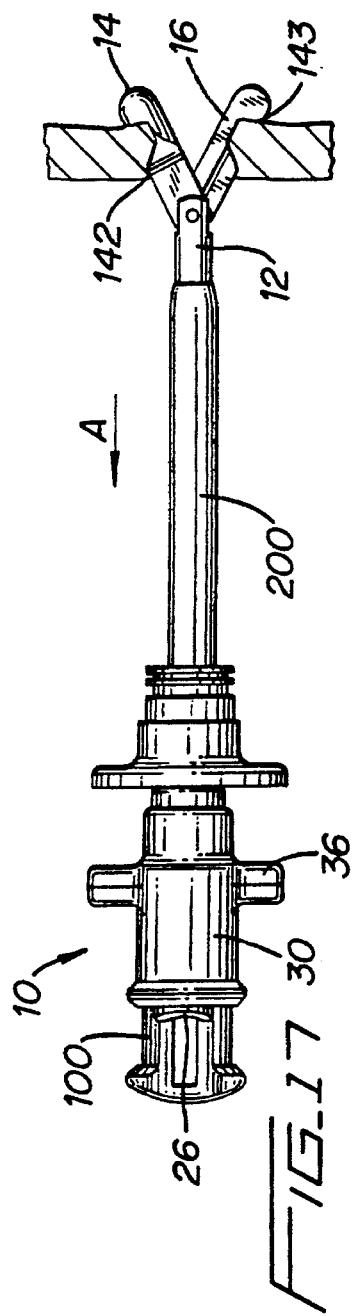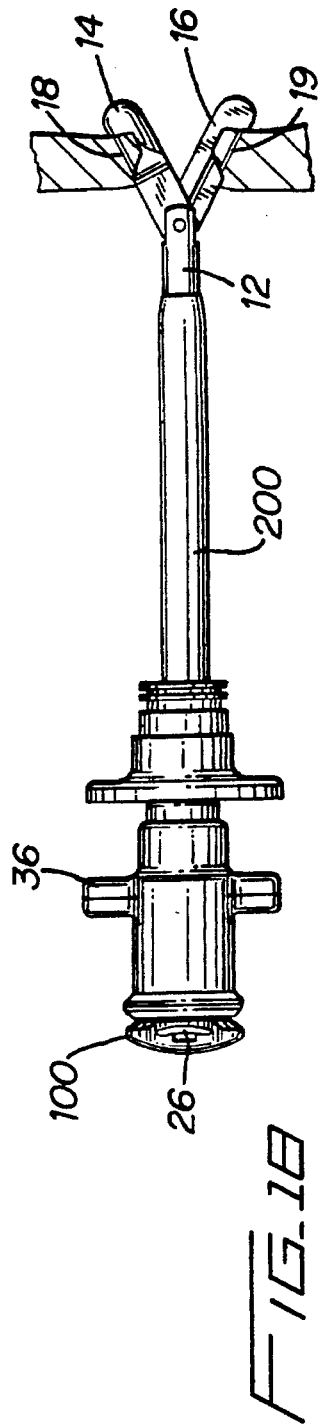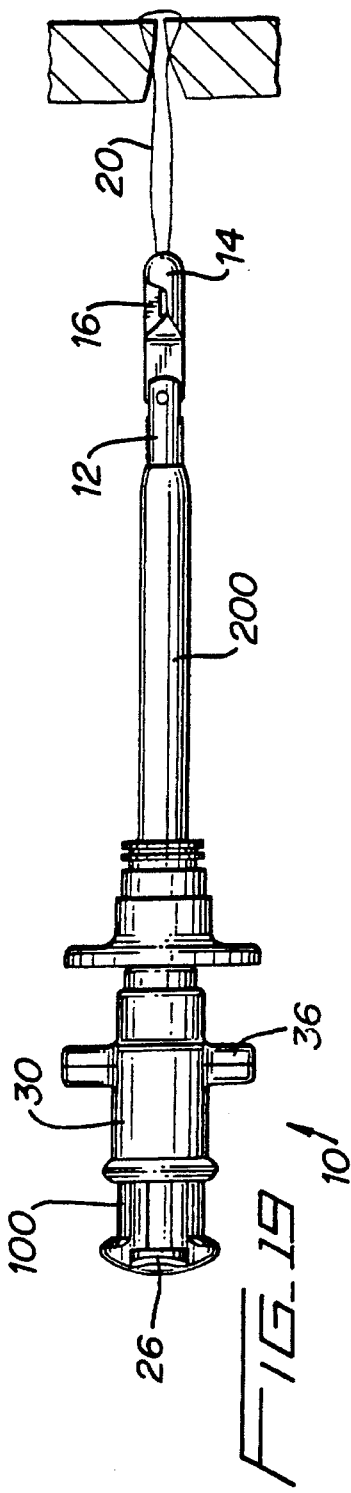

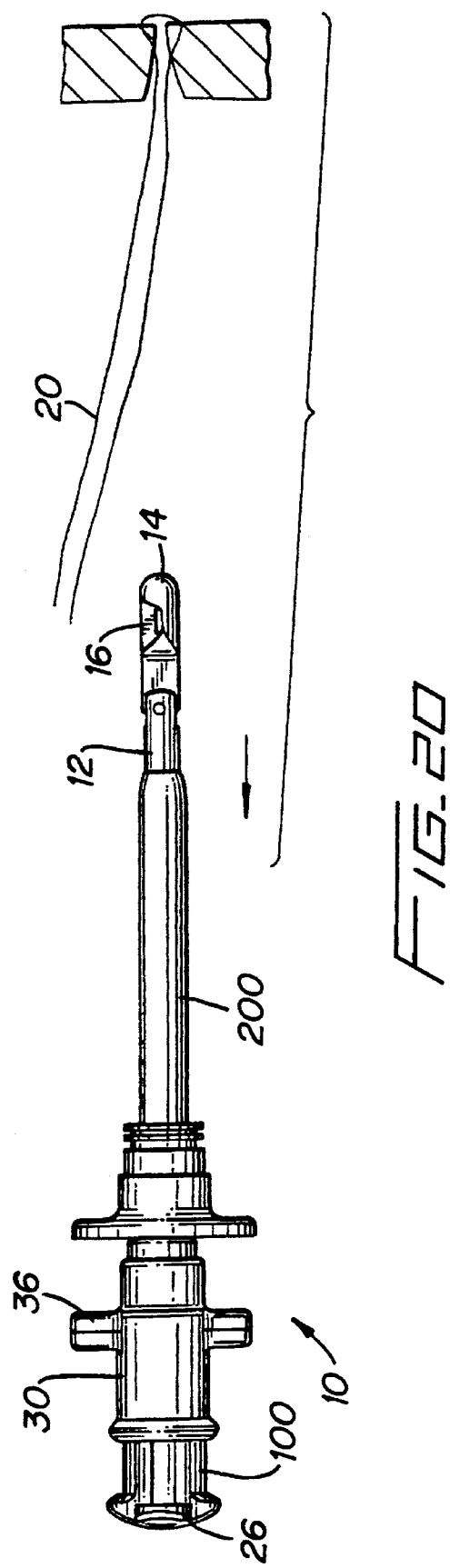
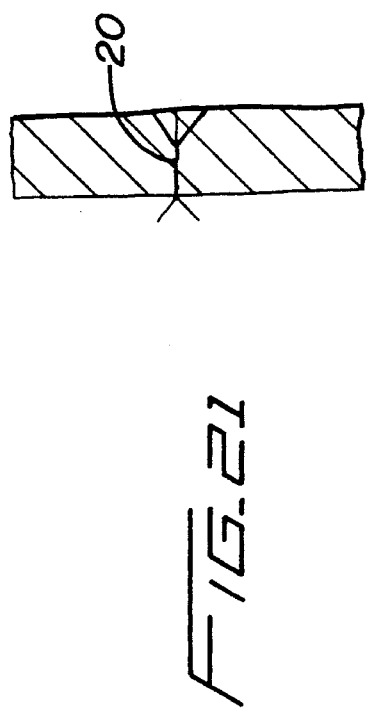
FIG. 20
FIG. 21

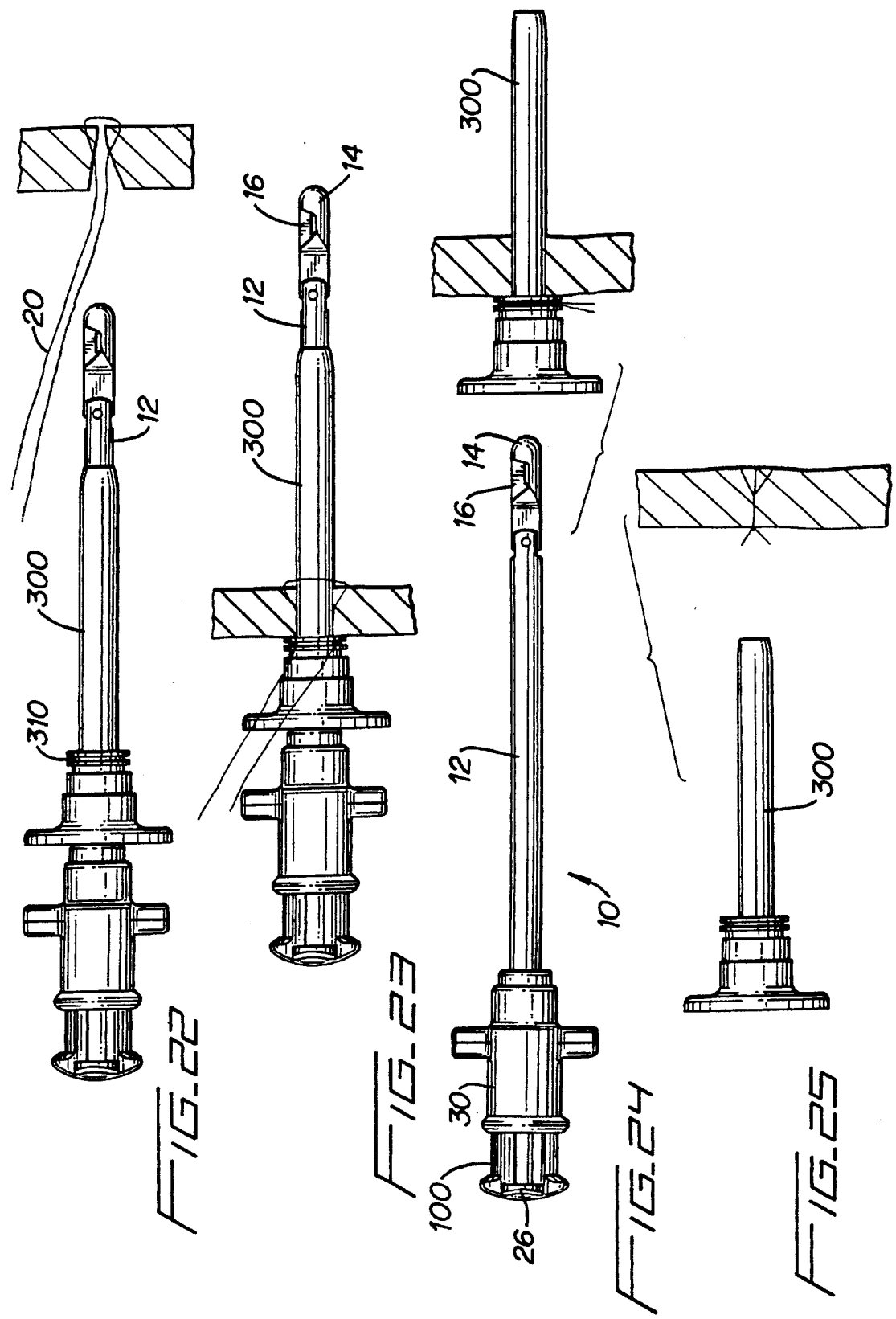

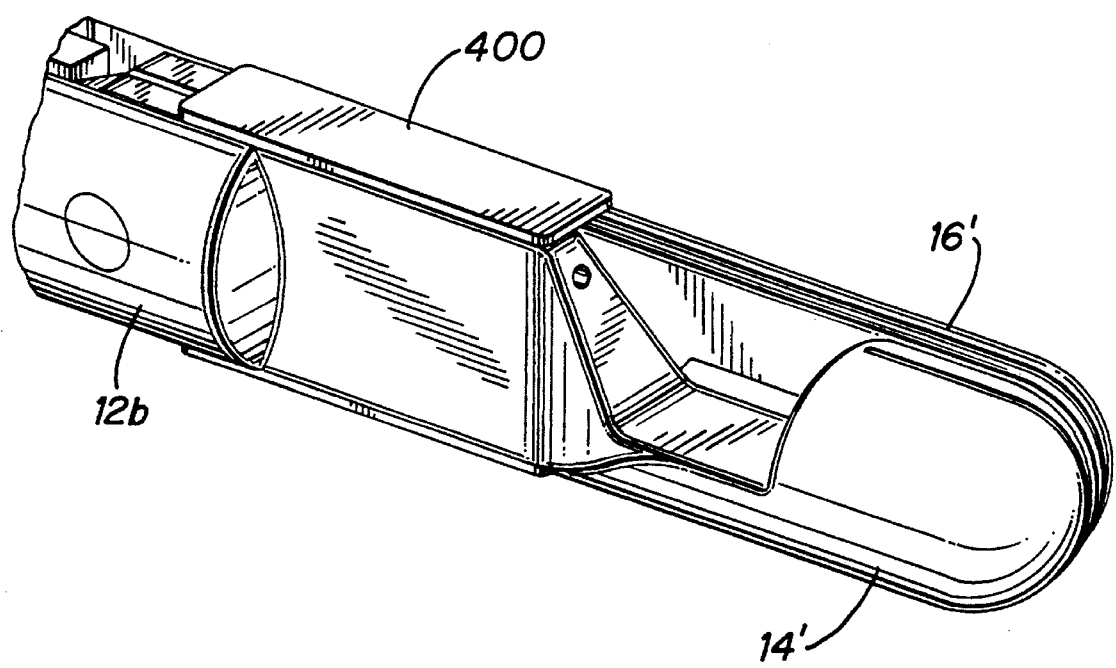

5,562,686

APPARAUS AND METHOD FOR SUTURING BODY TISSUE

BACKGROUND

Technical Field

This application relates to a surgical apparatus for suturing body tissue, and more particularly to an endoscopic apparatus for closing an incision created by a trocar.

Background of Related Art

Endoscopic and laparoscopic surgical procedures are performed through access ports or through small incisions in the body tissue. When performed through access ports, a plurality of trocars comprising an obturator with a sharp penetrating tip and a hollow cannula are inserted through the skin and underlying tissue layers into the body cavity. The obturator is then removed, leaving the cannula positioned in the body to provide an access port to the surgical site for introduction of a variety of surgical instruments such as staplers, clip appliers, scissors, retractors and graspers to perform the surgical procedure. At the end of the surgical procedure, the cannulas are withdrawn from the body tissue leaving an opening usually ranging from 5 to 20 millimeters, depending on the size of the cannula being used.

Typically, these trocar incisions are closed by the surgeon manually suturing the wound edges. However, such suturing does not always effectively close the lowermost layers of tissue, e.g., the muscle and fascia layers, thereby providing sub-standard wound closure.

Inadequate tissue re-approximation and subsequent poor healing of trocar sites can lead to wound closure defects in the abdominal wall. Abdominal contents, often bowel or mesentery, can bulge, (i.e. herniate) through such a defect.

Several attempts have been made to design instruments to effectively and expeditiously close trocar incisions. One such instrument is disclosed in U.S. Pat. No. 5,368,601 to Sauer. This instrument contains two needles which are deployed inside the body cavity with the pointed tips facing upwardly towards the skin. U.S. Pat. No. 5,320,632 to Heidmueller discloses a wound closure instrument having a pair of needles pointed upwardly and a slidable needle shield to capture the needle tips when pulled upwardly through the skin. Another type of wound closure device is disclosed in U.S. Pat. No. 5,364,482 to Gordon. In Gordon, a pair of curved needles are deployed from the apparatus in an arcuate path to penetrate the lowermost layers of the wound.

The need exists for an improved apparatus to close trocar incisions. It would be advantageous if the device effectively closed the lower muscle and fascia layers of the wound. It would also be advantageous if the device could effectively control and ensure proper placement of the suture in the desired position.

SUMMARY

An apparatus for suturing body tissue is disclosed comprising an elongated body portion, first and second jaws pivotably mounted to the distal portion of the body portion, and first and second needles movable with respect to the first and second jaws, respectively. A first actuator is operatively associated with the first and second jaws for moving the jaws from a first to a second position and a second actuator is operatively associated with the first and second needles for advancing the needles through the body tissue.

In the first position the jaws are closed and in a second position the jaws are spread apart to an acute angle with respect to the longitudinal axis of the body portion. Each of the jaws has a recess for receiving body tissue and a needle receiving member (a ferrule) mounted therein such that actuation of the second actuator advances the first and second needles into engagement with one of the ferrules. A suture is connected at each end to one of the ferrules such that advancement of the needles to engage the ferrules effectively connects the needles to the suture and retraction of the needles after such engagement pulls the ferrules and suture through the body tissue.

Preferably, the first actuator is longitudinally slidable and is operatively connected to an elongated plunger which is slid distally to cam the first and second jaws to the open position. The second actuator is also preferably longitudinally slidable and is operatively connected to first and second needle drivers (elongated rods) which are connected to first and second flexible mounting rods. The first and second flexible rods mount the first and second needles and are preferably composed of a superelastic material which enables movement at an acute angle with respect to the longitudinal axis of the elongated housing when the jaws are moved to their open position.

The apparatus preferably also includes a safety latch which prevents actuation of the second actuator if the jaws are not in the open position. The safety latch has a step portion engageable with a portion of the needle driving mechanism to block movement thereof if the jaw actuation mechanism has not been actuated to move the jaws to the open position. Sliding movement of the jaw actuation mechanism to open the jaws automatically cams the safety latch out of the blocking position to allow subsequent movement of the needle driving mechanism.

A method for closing a trocar wound is also disclosed comprising the steps of inserting an apparatus having first and second jaws and first and second needles into the body cavity through the trocar wound, spreading the first and second jaws to an open position, and advancing the first needle through the first jaw and the second needle through the second jaw to penetrate body tissue. The step of advancing the first and second needles includes the step of advancing the needles in a distal direction at an angle to the longitudinal axis to connect each needle to an end portion of a suture positioned in a distal end of the jaws. The step of connecting each needle to the suture includes the step of each needle frictionally engaging a ferrule connected to each end of the suture.

The method for closing the trocar wound further includes the step of retracting the needles after engagement with the ferrules, moving the jaws to the closed position, and withdrawing the apparatus from the body cavity to pull the suture through the tissue. The suture is then removed from the ferrules and a knot is formed in the suture outside the body cavity and the knot is secured at the level of the muscle in the trocar wound.

A method is also disclosed in which prior to tying a knot in the suture after the suture has been pulled through the body tissue, the suture is wrapped around a cannula fastening device to help retain the trocar cannula in position with respect to the body tissue during the surgical procedure. At the end of the surgical procedure, the suture is unwound from the cannula fastening device and tied outside the body cavity to close the trocar incision.

BRIEF DESCRIPTION OF THE DRAWINGS

Various embodiments of the surgical apparatus of the subject application will be described below with reference to the following drawings wherein:

FIG. 1 is a perspective view of the surgical apparatus for suturing body tissue;

FIG. 1A is an exploded perspective view of the apparatus of FIG. 1;

FIG. 2 is a cross-sectional view taken along lines 2—2 of FIG. 1 showing the jaws in the closed position and the needles in the retracted (non-deployed) position;

FIG. 3 is a cross-sectional view taken along lines 3—3 of FIG. 2 showing the jaw actuation mechanism in the proximalmost position corresponding to the closed position of the jaws and the needle driving mechanism in the proximalmost position corresponding to the retracted position of the needles;

FIG. 3A is a cross-sectional view taken along lines 3A—3A of FIG. 3 showing the engagement between the front and rear plungers of the jaw actuation mechanism;

FIG. 3B is a cross-sectional view taken along lines 3B—3B of FIG. 2 showing the jaws in the closed position and the needles in the retracted position;

FIG. 4 is a cross-sectional view taken along lines 4—4 of FIG. 3;

FIG. 5 is a cross-sectional view taken along lines 5—5 of FIG. 3 showing the connection of the plunger latch and the rear plunger;

FIG. 6 is a cross-sectional view taken along lines 6—6 of FIG. 3B;

FIG. 7 is a cross-sectional view similar to FIG. 3 with the jaw actuation mechanism in the advanced position to open the jaws and the needle driving mechanism in the proximalmost position, and also showing release of the safety latch to release the needle driving mechanism;

FIG. 7A is a cross-sectional view similar to FIG. 3B with the jaws in the open position and the needles in the retracted position;

FIG. 8 is a cross-sectional view taken along lines 8—8 of FIG. 7 showing retention of the plunger latch in the advanced position to retain the jaws in the open position;

FIG. 8A is a cross-sectional view similar to FIG. 8 showing release of the plunger latch by the driver stop during advancement of the needle driving mechanism;

FIG. 8B is a cross-sectional view taken along lines 8B—8B of FIG. 9 showing the engagement of the driver stop and the plunger latch when the needle driving mechanism is advanced to deploy the needles;

FIG. 9A is a cross-sectional view similar to FIG. 3B with the jaws in the open position and the needles in the deployed position;

FIG. 10 is an enlarged view of a portion of the jaw showing the ferrule prior to engagement by the needle;

FIG. 11 is an enlarged view of a portion of the jaw showing the frictional engagement of the needle and ferrule when the needles are advanced to the position shown in FIG. 9A;

FIG. 12 is a cross-sectional view taken along lines 12—12 of FIG. 9 showing the position of the drive pin in the elongated slot of the front plunger prior to retraction of the jaw actuation mechanism to close the jaws;

FIG. 12A is a view similar to FIG. 7A except showing retraction of the needles after engagement with the ferrules;

FIG. 12B is a cross-sectional view taken along lines 12B—12B of FIG. 12A illustrating the position of the drive pin when the needles have been retracted after engagement with the ferrules and the jaws are not yet returned to their closed position;

FIG. 13 is a cross-sectional view similar to FIGS. 3 and 3A except showing the needle driving mechanism and the jaw actuation mechanism returned to their initial position after engagement of the needles and ferrules;

FIG. 14 is a side view of the surgical suturing apparatus of FIG. 1 prior to introduction through a trocar cannula;

FIG. 15 is a side view illustrating the surgical apparatus inserted into the body cavity through the trocar cannula;

FIG. 16 is a side view illustrating the jaws of the apparatus deployed to the open position inside the body cavity;

FIG. 17 is a side view illustrating placement of the open jaws adjacent the tissue to be sutured;

FIG. 18 is a side view showing advancement of the needles through the body tissue;

FIG. 19 is a side view illustrating the surgical apparatus and trocar cannula removed from the body leaving a loop of suture positioned in the tissue;

FIG. 20 is a side view illustrating the apparatus separated from the suture;

FIG. 21 shows the suture tied to close the trocar incision;

FIGS. 22–25 illustrate an alternate method of use for the surgical apparatus in which FIGS. 22 and 23 illustrate the surgical apparatus re-inserted into the body cavity through a trocar cannula having a cannula mounting apparatus positioned thereon, FIG. 24 illustrates withdrawal of the surgical apparatus after the suture is wrapped around the cannula mounting device to retain the trocar cannula in position; and FIG. 25 illustrates the trocar cannula removed from the tissue and the suture tied to close the trocar incision; and FIG. 26 is a perspective view of an alternate embodiment of the jaws having a shield.

DETAILED DESCRIPTION OF THE PREFERRED EMBODIMENTS

Figure 9:
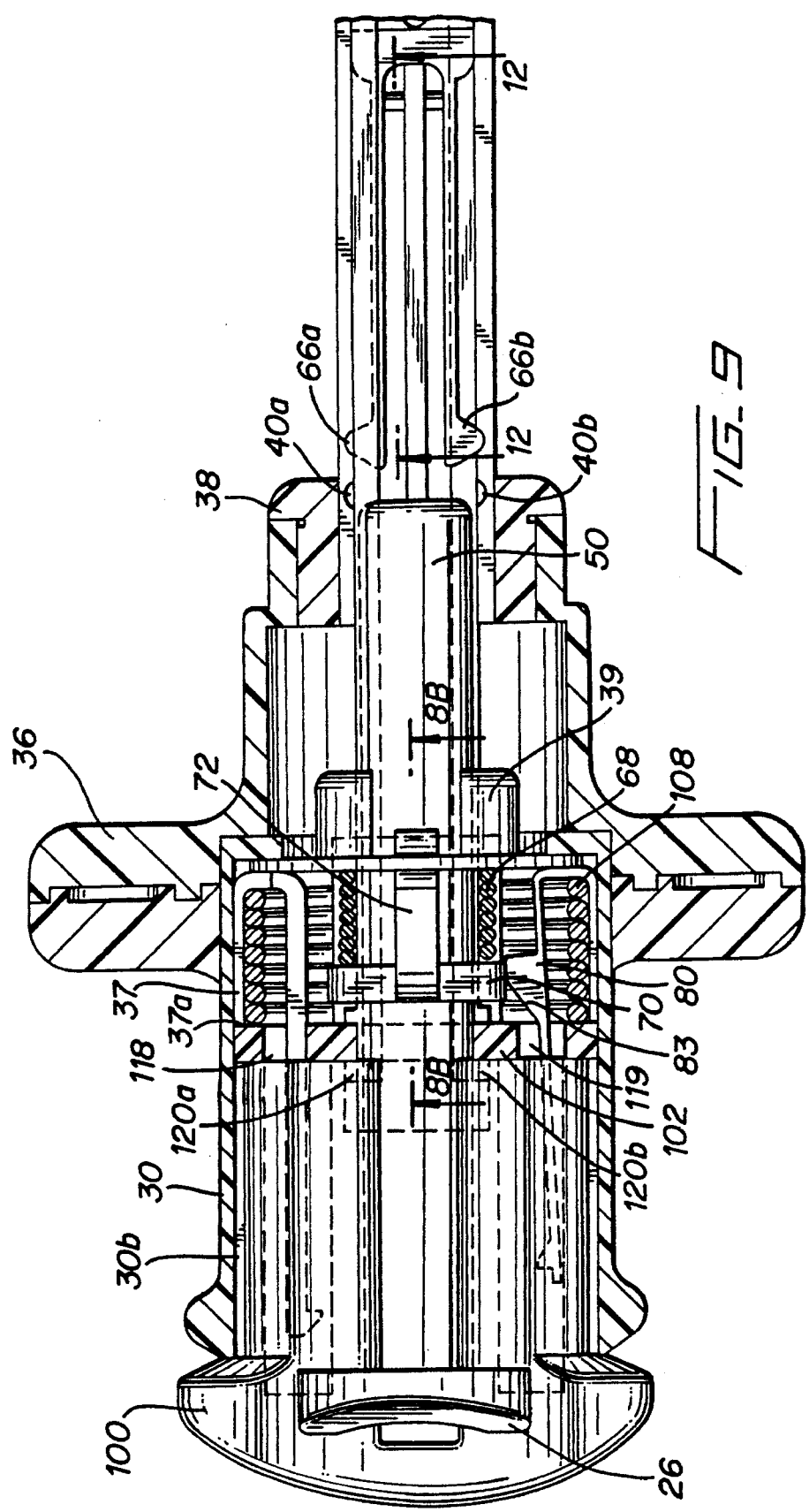
FIG. 9 is a cross-sectional view similar to FIG. 3 with the jaw actuation mechanism in the advanced position to open the jaws and the needle driving mechanism in the advanced position to deploy the needles.

Referring now to the drawings and in particular to FIG. 1, a surgical apparatus, designated generally by reference numeral 10, is provided for closing incisions in body tissue. During endoscopic or laparoscopic procedures, several trocars are inserted through the skin and underlying tissue layers into the body cavity. The trocar typically includes an obturator having a piercing tip and a hollow cannula. After insertion, the obturator is removed, leaving the cannula in place to provide an access port for endoscopic instruments such as staplers, clip appliers, graspers, scissors and other instruments necessary to perform the surgical procedure. In other minimally invasive procedures, the instruments may be inserted directly through the body tissue to access the surgical site without the use of a cannula. In either case, at the end of the surgical procedure, an incision remains through the underlying tissue layers, created by the trocar or by the direct insertion of the instruments, which the apparatus 10 disclosed herein is designed to close.

Referring to FIG. 1, the apparatus 10 has an elongated body portion or shaft 12 which is dimensioned for insertion through either a trocar cannula or directly into a small incision in the body tissue. A jaw actuation mechanism, which includes actuator 26, is slid forward (distally) to spread the jaws 14, 16 from the closed position of FIG. 1 to an open position. Once the jaws are properly placed adjacent the tissue to be sutured, a needle driving mechanism, which includes end cap 100, is pressed distally to advance a pair of surgical needles through the body tissue and into the distal end of the jaws. The needles each engage a ferrule connected at opposite ends to a suture and positioned in the distal end of the jaws. In this manner, when the needles are retracted to their initial position, they carry their associated ferrules and connected suture through the body tissue to place the suture on both sides of the trocar incision. The suture is then tensioned and manually tied from outside the body to approximate the tissue on both sides of the trocar incision and to close the incision.

Turning now to the individual components of the surgical suturing apparatus 10, and with reference to FIGS. 1A, 2, and 3, the housing portion of apparatus 10 includes a cap housing 30 which is mounted within a grip portion 34. A pair of wings 36 extend radially from grip portion 34 to facilitate grasping by the user. A bushing 38, Configured for supporting elongated body portion 12, is seated within a central bore 33 of grip portion 34. A detent washer 39 is positioned at a distal end of cap housing 30, in abutment with wall 30a, and is configured to facilitate retention of the rear, plunger of the jaw actuation mechanism described below.

The elongated body portion 12, composed of two body halves 12a, 12b, preferably has an outer diameter between approximately 10 and 15 millimeters, although other dimensions are also contemplated. A suture receiving channel 31 (see FIGS. 3B and 6) is formed in booth body halves for ease of manufacture, although suture 20 is positioned, as shown, in only one suture receiving channel 31. Proximal and distal detents 40a, 42a are formed in body half 12a and proximal and distal detents 40b and 42b are formed in body half 12b (see FIGS. 7 and 3) for the reasons described below.

Turning now to the jaw actuation mechanism and initially to FIG. 1A, the jaw actuation mechanism is movable between a retracted (proximalmost) position in which the jaws 14, 16 are maintained in the closed position and an advanced (distalmost) position in which the jaws 14, 16 are spread to an open position. The jaw actuating mechanism includes an actuator 26 in the form of a thumb pad, a rear plunger 50, a front plunger 54 and a plunger latch 70, all of which are movable between retracted and advanced positions. Plunger return spring 68 is mounted over rear plunger 50 and sandwiched between plunger latch 70 and detent washer 39 to bias the plunger latch 70 (and rear plunger 50) proximally to its retracted position.

Rear plunger 50 has a radially extending flange 52 at a proximal end for mounting thumb pad 26, and a distally extending flattened tongue 56 having an opening 58 to receive a drive pin 60.

Front plunger 54, as shown in FIG. 3A, has an elongated slot 64 formed at a proximal end to accommodate drive pin 60. A pair of projections 66a, 66b (FIG. 3), formed on arms 65, engage either the detents 40a, 40b or 42a, 42b in the shaft 12, depending on the longitudinal position of the plunger 54. That is, in the initial position of the plunger 54, projections 66a, 66b engage proximal detents 40a, 40b of body halves 12a, 12b to help maintain the jaws 14, 16 in the closed position. When the front plunger 54 is advanced to cam the jaws 14, 16 to the open position, projections 66a, 66b engage distal detents 42a and 42b to help maintain the jaws in the open position and provide a tactile feel to the user to indicate deployment of the jaws to the open position.

As shown in FIGS. 1A and 2, plunger latch 70 has a pair of longitudinally extending arms 72 terminating in retention tips 73 and a central aperture 74 dimensioned for reception of rear plunger 50. Mounting pin 75, as shown in FIGS. 1A and 5, extends through aperture 51 in rear plunger 50 and top and bottom openings of plunger latch 70 to connect plunger latch 70 to rear plunger 50. The plunger latch 70, which advances and retracts along with movement of the plungers 50, 54, functions to both lock the jaw actuating mechanism in the advanced position and to disengage the safety mechanism of the apparatus. This is described in detail below.

When thumb pad 26 is slid longitudinally distally, rear plunger 50, plunger latch 70, and front plunger 54 are likewise slid longitudinally distally. As the front plunger 54 is advanced, its distal abutting surface 62 (see FIG. 3B) contacts a rear surface of the jaws 14, 16 to cam them to the open position. FIGS. 2 and 3 show the thumb pad 26, rear plunger 50, front plunger 54 and plunger latch 70 in the proximalmost position with the jaws 14, 16 in the closed position; FIG. 7 illustrates the position of these elements when they are advanced to spread the jaws 14, 16 to the open position.

It is also contemplated that other mechanisms can be utilized for moving the jaws between open and closed positions. For example, the jaws can be provided with cam slots to receive a camming pin positioned on an actuating rod and a trigger or a pivotable handle mechanism instead of a slidable thumb pad could be utilized. Additionally, the jaws can alternately be normally biased in the open position such that actuation of the jaw actuation mechanism will close the jaws.

Turning now to the needle driving (actuating) mechanism, and initially to FIGS. 1A, 2 and 3, the needle driving mechanism is movable between a retracted (proximalmost) position wherein the needles 18, 19 are shielded within the jaws 14, 16 and an advanced (distalmost) position wherein the needles 18, 19 are advanced to penetrate body tissue. The needle driving mechanism includes an end cap 100, a driver stop 102, a pair of needle drivers 104a, 104b and a pair of mounting wires 106a, 106b for frictionally mounting needles 18, 19, respectively. A compression spring 108, sandwiched between detent washer 39 and driver stop 102, biases driver stop 102 (and end cap 100) proximally to its retracted position.

End cap 100, is slidably mounted with respect to cap housing 30 and has an axial bore 112 for receiving rear plunger 50, a groove 110 to accommodate flange 52 of rear plunger 50, and channels 111a, 111b to accommodate assembly latch 37 and safety latch 80 (described below) when the end cap 100 is slid distally within central bore 32 of cap housing 30. During advancement of thumb pad 26 to advance rear plunger 50 to open the jaws 14, 16, end cap 100 remains stationary as flange 52 slides within groove 110.

Driver stop 102 of the needle driving mechanism is seated within a proximal end of central bore 32 of cap housing 30, and has a proximal flange 116 which is frictionally mounted within axial bore 112 of end cap 100. A pair of legs 114, each having an indentation 120, extend distally from driver stop 102 and interact with arms 72 and retention tips 73 of plunger latch 70 in a manner described below. Top and bottom grooves 118, 119 are dimensioned to receive assembly latch 37 and safety latch 80 therethrough to allow unimpeded movement of driver stop 102. Top and bottom projections 107a, 107b are seated within channels 30b formed along the length of the inner surface of cap housing 30, as best seen in FIG. 4. Central opening 103 accommodates rear plunger 50.

Needle drivers in the form of elongated drive rods 104a, 104b are each mounted to driver stop 102 for movement therewith via proximal mounting flanges 120a and 120b which are snapped over the inner wall of driver stop 102 (see FIGS. 1A and 3). The distal forked ends 116a, 116b of needle drivers 104a, 104b frictionally engage mounting wires 106a, 106b, respectively. The needles 18, 19, are in turn frictionally mounted within a recess formed in wires 106a, 106b, respectively. Alternately, the needles can have a recess formed therein for frictionally mounting to the wires 106a, 106b. The mounting wires are preferably made of superelastic wire, such as Tinel or Nitinol wire, to allow flexing and bending to enable the needles to travel through the jaws 14, 16 when the jaws are positioned in their angular open position. Clearly other materials can also be utilized to enable the mounting wires to perform their function.

FIGS. 2 and 3 show the needle driving mechanism in the proximalmost position wherein head 101 of end cap 100 is spaced from cap housing 30, driver stop 102 is positioned within a proximal portion of cap housing 30, and needle drivers 104a, 104b and their respective mounting wires 106a, 106b and needles 18 and 19 are also in the retracted position. FIG. 9 illustrates the needle driving mechanism in the deployed position to advance the surgical needles 18, 19. As is apparent, when end cap 100 is pressed distally towards cap housing 30, driver stop 102 and connected needle drivers 104a, 104b, are also forced distally. This movement of the needle driving mechanism is described in more detail below.

Assembly latch 37 (FIGS. 1A and 3) has a leg 37b which extends through top groove 118 of driver stop 102 as shown in FIG. 3. Opposing leg 37a is fixed within annular channel 30b of cap housing 30, thereby functioning to connect driver stop 102 to the cap housing 30. Leg 37b enters channel 111a of end cap 100 when end cap 100 is slid distally.

Turning now to the jaws 14, 16 of the surgical apparatus 10, and with reference to FIGS. 1A, 3B and 7A, jaws 14, 16 are pivotably mounted to body portion 12 via pivot pin 132 extending through apertures 130. A tissue gap or recess portion 142 and 143, is formed in each jaw 14, 16 respectively, for receiving body tissue to be sutured. Angled proximal edges 146, 148 are configured so that engagement by abutment surface 62 of front plunger 54 cams the jaws to the open position of FIG. 7A. As shown, the jaws rotate about pin 132 in opposite directions.

Referring to FIG. 7A, a needle guide 133 with an exit opening 137 for the surgical needle 18 is formed proximal of recess portion 142 of jaw 14. Distal of recess portion 142 is an entrance opening 144, and a cutout for receiving oval shaped ferrule 24. A suture guide or groove 131 is formed in jaw 14 to accommodate suture 20. Jaw 16, is a mirror image of jaw 14, and as shown in FIG. 3B has a needle guide 136, an exit opening 138, an entrance opening 141, a cutout for receiving oval shaped ferrule 22 and a suture guide 134. Blunt ends 94, 95 of jaw 14, 16 are atraumatic and minimize trauma to body tissue during insertion and manipulation of the apparatus 10 in the body cavity.

As shown, in the open position, jaws 14 and 16 are positioned at an angle to the longitudinal axis of the elongated body portion 12. Preferably, the angle is an acute angle of approximately 30° as shown, however, clearly it is contemplated to deploy the jaws to various angles with respect to the longitudinal axis of the body portion.

In the non-deployed position of needles 18, 19 as shown in FIGS. 3B and 7A, needle 19 is seated within needle guide 136 and needle 18 is seated within needle guide 133 such that pointed tips 123, 125 are unexposed and not in contact with tissue. Note that in the closed position of the jaws of FIG. 3B, needle mounting wires 106a, 106b are substantially straight. When the jaws are moved to the open position of FIG. 7A, the mounting wires 106a, 106b bend at regions 106c, 106d, respectively. Consequently, when the jaws 14 and 16 are spread to their angular position with respect to shaft 12, mounting wires 106a, 106b bend at a similar angle.

Suture 20 is attached at one end to ferrule 22, wraps through the suture guide 134 in jaw 16, extends through central aperture 132a in pivot pin 132 and through suture guide 31 in body half 12a of shaft 12. The suture 20 is looped at the proximal end of suture guide 31 and extends back along the length of suture guide 31, back through central aperture 132a in pivot pin 132, around the suture guide 131 in jaw 14 and is attached at its other end to ferrule 24. Optionally, the suture guide can extend through an opening in the cap housing 30 so that it can be manually tugged to ensure that the ferrules 22, 24 are properly seated in their respective cutouts, the suture is snugly fit into suture guides 131, 134 and the remaining length of suture lies properly in suture guide 31. Extension of the suture through the cap housing also easily accommodates extra length of suture.

When the needle driving mechanism is actuated, and needle drivers 104a, 104b are advanced distally, superelastic mounting wires 106a, 106b are also forced distally along the nonlinear path formed by the open jaws 14, 16 to force the needles 18, 19 out of exit openings 137, 138, through the body tissue seated in recesses 142, 143, and into entrance openings 144, 141 of jaws 14, 16. As the needles 18, 19 are advanced through entrance openings 144, 141, they frictionally engage ferrules (needle engaging members) 24, 22 positioned in the cutouts in the jaws. As a result, the surgical needles 18, 19 effectively become connected to the suture 20. (see FIGS. 9a and 11) Thus, when the needles 18, 19 are retracted back through exit openings 137 and 138 and into needle guides 133, 136, the frictional engagement of the needle tips 125, 123 with the ferrules 24, 22 pulls the ferrules and attached suture 20 proximally through the tissue and into the needle guides 133, 136 as shown in FIG. 12A. Note that a mechanical engagement instead of a frictional engagement between the ferrules and needles is also contemplated.

The apparatus 10 also includes a safety mechanism which prevents deployment of the needles 18, 19 if the jaws 14, 16 have not first been moved to the open position. More particularly, the safety mechanism includes a safety latch 80 in the form of a spring which is normally in the position illustrated in FIG. 3. Leg 84 is fixed within annular channel 30b of cap housing 30. Step 82 is positioned at the proximal end of latch 80 and in the initial position abuts wall 102b of driver stop 102. In this initial blocking position of FIG. 3, if the user attempts to press end cap 100 distally to advance the needles, wall 102b of driver stop 102 will contact step 82 of safety latch 80 and be blocked from distal movement.

Safety latch 80 is automatically moved from a blocking to a non-blocking position upon advancement of the jaw actuating mechanism. More specifically, when plunger 50 is advanced to move the jaws to the open position, as shown in FIG. 7, the base portion 71 of plunger latch 70 contacts ramp surface 83 of safety latch 80 and forces it downwardly such that step 82 is cammed out of engagement with the wall 102b of driver stop 102. In this non-blocking position of FIG. 7, step 82 is aligned with groove 119 of driver stop 102 and allows for free movement thereof. Consequently, when end cap 100 is pressed inwardly to deploy the needles, driver stop 102 can likewise travel distally as groove 119 passes over step 82. Thus, driver stop 102 and the associated components of the needle driving mechanism can be advanced to the position of FIG. 9 to deploy the needles.

The use of the apparatus will now be described. In the initial position, the jaws 14, 16 are in the closed position and the needles 18, 19 are in the retracted position within jaws 14, 16. In this initial position shown in FIGS. 2, 3 and 3B, thumb pad 26, rear plunger 50, front plunger 54 and plunger latch 70 are in the retracted (proximalmost) position. Note in this initial position, the raised surfaces of retention tips 73 of plunger latch 70 are nested in recesses 120 of legs 114 of driver stop 102, compression springs 68 and 108 are in the preloaded positions as shown, and projections 66a and 66b of front plunger 54 are positioned in rear detents 40a, 40b of elongated body portion 12. Also, in this initial position, end cap 100, driver stop 102, needle drivers 104a, 104b, and needle mounting wires 106a, 106b are in the proximalmost position and are prevented from movement due to the abutment of wall 102b of driver stop 102 and step 82 of safety latch 80.

When the apparatus 10 is positioned in the body cavity and the user wishes to deploy the jaws 14, 16 to the open position, thumb pad 26 is slid distally thereby forcing rear plunger 50, plunger latch 70 and front plunger 54 distally to the advanced (distalmost) position of FIGS. 7 and 7A, compressing spring 68. Note that, as plunger latch 70 is slid distally, wall 71 contacts the ramp 83 of safety latch 80 to cam step 82 out of engagement with driver stop 102 in the manner described above. This frees the needle driving mechanism for advancement. As plunger 54 is advanced, its abutment surface 62 contacts angled edges 146, 148 of jaws 14, 16 and cams the jaws in opposite directions to the open position of FIG. 7A. In this distal position of front plunger 54, projections 66a 66b engage distal detents 42a, 42b of elongated body portion 12 and retention tips 73 of plunger latch 70 engage an inner wall 39a (FIG. 8) of detent washer 39 as shown. This engagement of plunger latch 70 with the fixedly positioned washer 39 effectively retains the plunger latch 70 (and the entire jaw actuation mechanism) in the advanced position, thereby ensuring that the jaws 14, 16 remain open during actuation of the needle driving mechanism.

When the apparatus is in the desired position with the body tissue seated in the recessed portions 142, 143 of opened jaws 14, 16, end cap 100 is pressed inwardly (distally) into cap housing 30, as shown in FIG. 9, thereby forcing driver stop 102, and the needle drivers 104a, 104b connected thereto distally and compressing spring 108. Note that movement of driver stop 102 is unimpeded by safety latch 80 because groove 119 is aligned with step 82. Channels 111a, 111b of end cap 100 and grooves 118, 119 of driver stop 102 accommodate assembly latch 37 and safety latch 80 to allow free travel of end cap 100 and driver stop 102. Top and bottom projections 107a, 107b of driver stop 102 travel along annular channel 30b of cap housing 30.

Advancement of needle drivers 104a, 104b advances mounting wires 106a, 106b and mounted needles 18, 19. Mounting wires 106a, 106b follow the acute angle of the jaws and force the needles 18, 19 through the body tissue positioned in the recess portions 142, 143 and into the entrance openings 144, 141 of jaws 14, 16 to frictionally engage the ferrules 24, 22. (see FIGS. 9A and 11) Consequently, needles 18 and 19 become connected to the suture 20.

Note that as shown in FIG. 8A, as driver stop 102 advances distally, it contacts the distal ends of arms 72 of plunger latch 70 to cam retention tips 73 out of engagement with inner wall 39a of detent washer 39 to thereby release plunger latch 70 to allow subsequent retraction. When driver stop 102 reaches its distalmost position, as shown in FIG. 8B, the projections of arms 72 of plunger latch 70 become re-nested in the indentations 120 of legs 114 of driver stop 102.

After the needles 18, 19 have been deployed into engagement with ferrules 24, 22, to retract the needles 18, 19 to pull the suture 20 through the body tissue seated into the recess portions of the jaw 14, 16 and to close the jaws to remove the instrument, end cap 100 is released and compression spring 108 forces it proximally to its initial position. As the end cap 100, driver stop 102 and associated needle drivers 104a, 104b and mounting wires 106a, 106b are retracted to pull the needles 18, 19 and ferrules 24, 22 into the exit openings 137, 138 of the jaws 14, 16, the plunger latch 70 and connected rear plunger 50 are also retracted due to the nesting of plunger latch 70 and driver stop 102 and the biasing force of compression spring 68. (Detents 42a, 42b help keep front plunger 54 in place while rear plunger 50 is moving proximally.) However, although rear plunger 50 is forced proximally toward its initial position, front plunger 54 does not move initially due to the interaction of plunger drive pin 60 and elongated slot 64 of front plunger 54. This ensures that the needles 18, 19 are fully retracted within jaws 14, 16 before the jaws are closed.

More specifically, with reference to FIGS. 12 and 12b, as rear plunger 50 moves proximally, drive pin 60 travels proximally in slot 64 of front plunger 54. During this dwell period, the front plunger 54 remains stationary. When the rear plunger 50 is retracted sufficiently so that drive pin 60 is at the proximalmost portion of the elongated slot 64 as shown in FIG. 12B, continued retraction of rear plunger 50 carries front plunger 54 to its initial position. In this initial position, the projections 66a, 66b re-engage the proximal detents 40a, 40b of the elongated body portion 12 to help retain the jaws in the closed position and to provide tactile indication to the user that the jaws are closed. Consequently, the jaw actuation and needle driving mechanisms are returned to the position of FIG. 13. Note that this position is identical to that of FIG. 3, except that the ferrules 24, 22 are now positioned in the needle guides 133, 136 of jaws 14, 16 and the suture 20 has been pulled across the recess portions 142, 143 through the body tissue. As can be seen in FIG. 13, the retraction of plunger latch 70 allows safety latch 80 to return to its original blocking position to block the driver stop 102.

FIGS. 14–21 illustrate the use of the surgical suturing apparatus 10 for closing an incision created by a trocar during an endoscopic/laparoscopic procedure. During endoscopic procedures, where surgery is performed inside the body cavity, one or more trocars are inserted through the body tissue to access the body cavity. A typical trocar includes an obturator having a sharp penetrating tip removably mounted within a cannula. After insertion of the trocar into the body cavity, the obturator is removed leaving the cannula in place to provide an access port for the insertion of various surgical instruments for performing the endoscopic/laproscopic surgical procedure. FIG. 14 illustrates the trocar cannula 200 positioned in the body tissue and the apparatus 10 prior to insertion therethrough.

When it is desired to close the incision created by the trocar, the surgical apparatus 10 is inserted through the trocar cannula 200 as illustrated in FIG. 15.

Once inside the body cavity, thumb pad 26 of the jaw actuation mechanism is slid distally as shown in FIG. 16 to advance the front plunger in the manner described above to spread the jaws 14, 16 to the open position. Both the trocar cannula 200 and the apparatus 10 are then pulled proximally in the direction of arrow A of FIG. 17 until the body tissue is seated within recess portions 142, 143 of jaws 14 and 16.

End cap 100 of the needle driving mechanism is then slid distally to advance the needle drivers in the manner described above to advance needles 18 and 19 through the body tissue to engage the ferrules in jaws 14 and 16.

After deployment of the needles 18, 19, end cap 100 is released to retract needles 18 and 19 and connected ferrules into the needle guides in the jaws 14 and 16 and allowing the jaw actuation mechanism to retract to pivot the jaws back to their initial closed position. As the needles 18, 19 are retracted, they pull the ferrules and suture 20 through the body tissue seated in the recessed portions in the manner described above.

The instrument 10 and trocar cannula 200 are then withdrawn together from the body tissue leaving a loop of suture adjacent the innermost tissue layer, e.g. the abdominal fascia, and the suture on both sides of the wound (extending through the fascia and muscle) as shown in FIG. 19. Suture 20 is cut at both ends or pulled (tugged) to separate it from the ferrules (FIG. 20), with the ferrules preferably releasing from the needles before the suture pulls out of the ferrules. Suture 20 is then tensioned to approximate the wound edges and a knot is tied to close the incision as shown in FIG. 21. Consequently, the incision is closed without penetrating the skin layer. Staples and/or separate suture can be manually placed through the skin and closed in the normal fashion.

The jaws may optionally be provided with a shield to maintain pneumoperitoneum and minimize the amount of effluent from the trocar wound when the jaws are retracted to their original position. The shield provides continuity of the apparatus seal to the abdominal wall, even when the jaws are opened and pulled into the wound site. The "spit" shield can be composed of a rigid or flexible material. FIG. 26 illustrates one example of a shield 400 positioned on jaw 16' and overlapping jaw 14'. The shield can alternately include a "skirt" of materiel that resides between the jaws inside the wound, or a gasket on the outside of the wound.

In an alternate use of the apparatus 10 illustrated in FIGS. 22–25, the suture 20 contained in apparatus 10 is used not only to close the trocar incision but to retain a trocar cannula in position with respect to the body tissue during the surgical procedure. The suture 20 is placed in the body tissue, the trocar cannula 300 and apparatus 10 are removed, and the ferrules are separated from the suture in the same manner as discussed above and as shown in FIG. 20. However, instead of tying the suture to close the incision, the apparatus 10 and trocar cannula 300 are re-inserted into the incision, with the apparatus 10 serving as a guide for the cannula 300. The cannula 300 in this embodiment, has either a circumferential groove for accommodating the suture or a separately mounted cannula ring fastening system such as the type described in European Patent Application No. 93115246.6, filed Sep. 22, 1993, the contents of which are incorporated herein by reference.

After the apparatus 10 and cannula 300 are re-inserted, the apparatus 10 is withdrawn from the cannula 300 and the suture 20 is wrapped around the circumferential groove 310 as shown in FIG. 24. The cannula 300 is then used as an access port for the insertion of the desired endoscopic/laparoscopic instruments to perform the surgical procedure. At the end of the procedure, when it is desired to withdraw the cannula and close the trocar incision, the suture is unwrapped from the groove 310 and the trocar cannula 300 and cannula ring fastener are removed. The suture is tied to approximate the wound edges and close the trocar incision as shown in FIG. 25.

It is also contemplated that the apparatus 10 described herein can be reloadable. That is, after the suture is applied to the body tissue, the ferrules can be removed from the needle tips and a fresh suture with a ferrule attached at each end can be loaded into the jaws of the apparatus. This would enable the apparatus to be used to close a plurality of trocar incisions using the same pair of needles. This embodiment could be provided to the user packaged as a kit with a single sterilized apparatus and several suture/ferrule arrangements. The sutures in the kit could be composed of different material, e.g. absorbable and nonabsorbable, so the user could select the desired material.

It should also be understood that the apparatus described herein can be used for closing other wounds and suturing other body tissue in addition to the above-described trocar incisions.

It will further be understood that various modifications may be made to the embodiments disclosed herein. For example, the jaw actuation mechanism and needle driving mechanism could be biased in a distal direction. Additionally, other mechanisms for opening and closing the jaws, e.g. cam slot and camming pin arrangement, as well as other mechanisms for deploying the needles could be provided. Therefore, the above description should not be construed as limiting but merely as exemplifications of preferred embodiments. Those skilled in the art will envision other modifications within the scope and spirit of the claims appended hereto.

What is claimed:

1. An apparatus for suturing body tissue comprising:
    an elongated body portion having a proximal and distal portion and defining a longitudinal axis;
    first and second jaws movably mounted to the distal portion of the elongated body portion;
    first and second needles movable with respect to the first and second jaws, respectively;
    a first actuator operatively associated with the first and second jaws, wherein actuation of the first actuator moves the jaws from a first position substantially aligned with each other to a second position substantially non-aligned with each other; and
    a second actuator operatively associated with the first and second needles, wherein actuation of the second actuator advances the first and second needles into body tissue, the second actuator being capable of advancing the first and second needles when the jaws are in the second position.

2. An apparatus for suturing body tissue according to claim 1, wherein in the first position the jaws are closed and in the second position the jaws are spread apart to an angle with respect to the longitudinal axis of the body portion.

3. An apparatus for suturing body tissue according to claim 2, further comprising first and second flexible rods operatively connected to the second actuator to drive the first and second needles distally into body tissue, a portion of the rods movable to an angle with respect to the longitudinal axis of the body portion when the jaws are moved to the open position.

4. An apparatus for suturing body tissue according to claim 2, wherein each of the jaws has an recess for receiving body tissue.

5. An apparatus for suturing body tissue according to claim 2, wherein in the second position the jaws are in an open position, and further comprising a safety latch, wherein the safety latch prevents actuation of the second actuator if the jaws are not in the open position.

6. An apparatus for suturing body tissue according to claim 5, further comprising a driver member operatively connected to the first actuator, wherein the safety latch has a blocking surface engagable with a portion of the driver member to block movement thereof if the first actuator has not been actuated to move the jaws to the open position, wherein sliding movement of the first actuator to open the jaws automatically cams the safety latch out of blocking engagement with the driver member.

7. An apparatus for suturing body tissue according to claim 1, wherein the first actuator is slidable longitudinally to move the jaws between the first and second position.

8. An apparatus for suturing body tissue according to claim 7, further comprising an elongated plunger operatively connected to the first actuator, such that movement of the first actuator longitudinally distally causes a distal end of the plunger to cam the first and second jaws to the second position, wherein in the second position the jaws are spread apart.

9. An apparatus for suturing body tissue according to claim 8, wherein the second actuator is slidable longitudinally and is operatively connected to first and second elongated rods, the first and second rods being operatively connected to the first and second needles, respectively.

10. An apparatus for suturing body tissue according to claim 1, wherein the second actuator is slidable longitudinally to advance the first and second needles distally.

11. An apparatus for suturing body tissue according to claim 10, further comprising first and second elongated rods operatively connecting the second actuator and the first and second needles.

12. An apparatus for suturing body tissue according to claim 1, wherein each of the jaws has a recess portion for receiving body tissue, a needle guide positioned proximally of the recess portion, and a needle engaging member positioned distally of the recess portion and attached to a suture.

13. An apparatus for suturing body tissue according to claim 12, wherein said first and second needles are configured and dimensioned such that upon movement of the second actuator, each needle is forced from the needle guide, through body tissue positionable in the recess portion, and into frictional engagement with the needle engaging member.

14. An apparatus for suturing body tissue according to claim 13, wherein said first and second needles are further configured and dimensioned such that upon return of the second actuator to a retracted position, each needle pulls the engaged needle engaging member proximally.

15. An apparatus for suturing body tissue according to claim 14, wherein the suture extends within a slot formed in an outer surface of each jaw and within the elongated body portion.

16. An apparatus for suturing body tissue according to claim 12, further comprising a shield positioned on at least one of the jaws to reduce the amount of effluent from the surgical site.

17. An apparatus for suturing body tissue comprising;

an elongated body portion having a proximal and distal portion and defining a longitudinal axis;

first and second jaws movably mounted to the distal portion of the elongated body portion;

first and second needles movable with respect to the first and second jaws, respectively;

a first actuator operatively associated with the first and second jaws, wherein actuation of the first actuator moves the jaws from a first position wherein the jaws are closed to a second position wherein the jaws are spread apart to an angle with respect to the longitudinal axis of the body portion;

a second actuator operatively associated with the first and second needles, wherein actuation of the second actuator advances the first and second needles into body tissue; and a first ferrule positioned in the first jaw and a second ferrule positioned in the second jaw, and a suture connected at one end to the first ferrule and connected at the other end to the second ferrule, wherein actuation of the second actuator to advance the first and second needles advances the first needle into engagement with the first ferrule and the second needle into engagement with the second ferrule.

18. An apparatus for suturing body tissue comprising:

an elongated body portion defining a longitudinal axis and having a proximal end portion and a distal end portion;

first and second needles movable with respect to the elongated body portion, the first and second needles being movable in a distal direction and at an angle relative to each other to penetrate body tissue; and a suture associated with said elongated body portion initially spaced from the first and second needles, wherein movement of the first and second needles distally connects the first and second needles to the suture.

19. An apparatus for suturing body tissue according to claim 18, wherein the suture is connected at each end to a ferrule such that movement of the first and second needles distally moves the needles into engagement with the ferrule to thereby connect the first and second needles to the suture.

20. An apparatus for suturing body tissue according to claim 19, further comprising a pair of elongated drive rods operatively connected to the needles, the drive rods actuable from the proximal end portion of the elongated body portion for moving the needles distally.

21. An apparatus for suturing body tissue according to claim 20, further comprising a pair of jaws pivotably mounted to the elongated body portion, wherein each of the jaws contains one of the ferrules.

22. An apparatus for suturing body tissue according to claim 20, wherein the ferrules and suture are removably and replaceably positioned in the apparatus and can be replaced with fresh ferrules and suture.

23. An apparatus for suturing body tissue comprising:

an elongated body portion;

first and second jaws extending from a distal end portion of the elongated body portion and mounted for relative movement with respect to one another between an open and closed position;

first and second needles movable with respect to the first and second jaws;

wherein the needles are movable in a distal direction to penetrate body tissue when the first and second jaws are disposed in the open position.

24. An apparatus for suturing body tissue according to claim 23, further comprising at least one suture, wherein movement of the needles in a distal direction connects the needles to the at least one suture.

25. An apparatus for suturing body tissue according to claim 24, further comprising a first longitudinally slidable actuating mechanism for moving the first and second jaws and a second longitudinally slidable driving mechanism for moving the first and second needles.

26. A method for closing trocar wounds comprising:
   a) inserting an apparatus having first and second jaws and first and second needles into the body cavity through the trocar wound;
   b) spreading the first and second jaws of the apparatus to an open position;
   c) advancing the first needle through the first jaw and the second needle through the second jaw to penetrate body tissue.

27. A method for closing trocar wounds according to claim 26, wherein the step of advancing the first and second needles includes the step of advancing the needles in a distal direction.

28. A method for closing trocar wounds according to claim 27, wherein the step of advancing the needles includes the step of advancing the needles distally at an angle to a longitudinal axis of the apparatus.

29. A method for closing trocar wounds according to claim 28, wherein the step of advancing the first and second needles includes the step of connecting each needle to a portion of a suture positioned in a distal end portion of the jaws.

30. A method for closing trocar wounds according to claim 29, wherein the step of connecting each needle to a portion of the suture includes frictionally engaging each needle to a ferrule connected to the suture.

31. A method for closing trocar wounds according to claim 30, further comprising the steps of:
   a) moving the jaws to the closed position;
   b) withdrawing the apparatus from the body cavity to pull the suture through the tissue;
   c) removing the suture from the ferrules; and
   d) forming a knot in the suture outside the body cavity.

32. A method for closing trocar wounds according to claim 31, wherein the step of inserting the apparatus through the body cavity includes the step of inserting the apparatus through a trocar cannula positioned in the trocar opening.

33. A method for closing trocar wounds according to claim 30, further comprising the steps of:
   a) moving the jaws to the closed position;
   b) withdrawing the apparatus from the body cavity to pull the suture through the body tissue;
   c) removing the suture from the ferrules; and
   d) wrapping the suture around a cannula fastening device.

34. A method for closing trocar wounds according to claim 33, further comprising the step of reinserting the apparatus into the body cavity prior to the step of wrapping the suture.

* * * * *